United States Patent [19]

Sandell

[11] Patent Number: 4,599,412

[45] Date of Patent: Jul. 8, 1986

[54] PROCESS FOR PREPARATION OF SULFONYLUREA SOLUTION FORMULATIONS

[75] Inventor: Lionel S. Sandell, Wilmington, Del.

[73] Assignee: E. I. Du Pont de Nemours and Company, Wilmington, Del.

[21] Appl. No.: 714,508

[22] Filed: Mar. 21, 1985

Related U.S. Application Data

[63] Continuation-in-part of Ser. No. 554,787, Nov. 23, 1983, abandoned.

[51] Int. Cl.$^4$ ............... C07D 251/41; C07D 251/46; C07D 239/69

[52] U.S. Cl. ................... 544/211; 544/212; 544/321; 544/320; 544/331; 544/332; 71/93; 71/92; 260/96.5 R; 260/96.5 C

[58] Field of Search ............... 544/211, 212, 321, 320, 544/331, 332; 71/93, 92; 260/96.5 R, 96.5 C

[56] References Cited

U.S. PATENT DOCUMENTS 4,127,405 11/1978 Levitt .................................. 544/211
4,169,719 10/1979 Levitt .................................. 71/93

Primary Examiner—John M. Ford

[57] ABSTRACT

The process of making a solution formulation of a sulfonylurea compound which includes contacting the formulation with molecular sieves to provide improved chemical stability to the solution formulation.

32 Claims, No Drawings

PROCESS FOR PREPARATION OF SULFONYLUREA SOLUTION FORMULATIONS

PRIOR APPLICATIONS

This application is a continuation-in-part of application Ser. No. 554,787 filed Nov. 23, 1983, now abandoned.

BACKGROUND OF THE INVENTION

The invention relates to a novel process for the preparation of solution formulations of sulfonylureas with improved chemical stability. Such formulations have enhanced storage life and are useful as pre-emergent or post-emergent herbicides and plant growth regulants.

U.S. Pat. Nos. 4,127,405 issued Nov. 28, 1978, and 4,169,719 issued Oct. 2, 1979, both patents to Levitt, disclose certain sulfonylurea compounds and processes for their preparation.

U.S. Application Ser. No. 482,025, filed Apr. 4, 1983, now abandoned discloses aqueous suspensions of sulfonylurea salts stabilized by insolubilization with salts of carboxylic acids or inorganic acids.

SUMMARY OF THE INVENTION

This invention relates to a novel process for the preparation of solution formulations of sulfonylureas of Formula I with improved chemical stability by contacting said solutions with molecular sieves. The sulfonylurea of Formula I is dissolved in a suitable non-reactive solvent which allows for a concentration of at least 0.5 weight percent. The formulation may optionally contain dissolved surfactants. The solution is stirred with molecular sieves for at least several minutes, or is percolated through a column of molecular sieves. The formulation is then either separated from the sieves or stored permanently over the sieves. This invention also relates to the novel solution formulations of sulfonylureas of Formula I prepared by the aforementioned process.

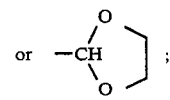

wherein
R is

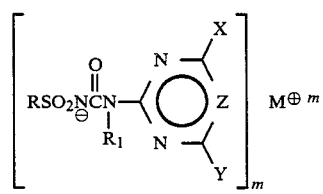

$R_1$ is H or $CH_3$;
$R_2$ L is F, Cl, Br, $C_1$-$C_4$ alkyl, $SO_2NR_6R_7$, $S(O)_nR_8$, $SO_2NCH_3(OCH_3)$, $CO_2R_9$, $OSO_2R_{10}$,

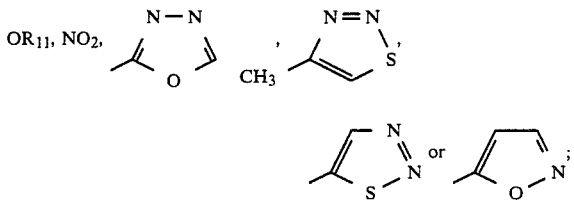

$R_3$ is H, F, Cl, Br, $CH_3$, $OCH_3$ or $CF_3$;
$R_4$ is Cl, $NO_2$ or $CO_2R_{10}$;
$R_5$ is Cl, Br, $SO_2NR_6R_7$, $S(O)_nR_{10}$ or $CO_2R_{10}$;
$R_6$ and $R_7$ are independently $C_1$-$C_3$ alkyl;
$R_8$ is $C_1$-$C_3$ alkyl or $C_1$-$C_3$ alkyl substituted by 1-5 atoms of F, Cl or Br;
$R_9$ is $C_1$-$C_4$ alkyl, $CH_2CH_2OCH_3$, $CH_2CH_2Cl$ or $CH_2CH=CH_2$;
$R_{10}$ is $C_1$-$C_3$ alkyl;
$R_{11}$ is $C_1$-$C_4$ alkyl, $CH_2CH=CH_2$, $CH_2C\equiv CH$ or $C_1$-$C_3$ alkyl substituted with 1-5 atoms of F, Cl or Br;
n is 0 or 2;
M is an agriculturally suitable cation;
m is 1, 2 or 3;
Z is CH or N;
X is $CH_3$, $OCH_3$, CL or $OCHF_2$; and
Y is $CH_3$, $OCH_3$, $CH(OCH_3)_2$, $OCHF_2$

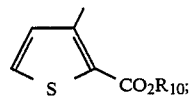

provided that when
X is Cl, then Z is CH and Y is $OCH_3$, or $OCF_2H$.
Preferred for the greater stability and/or greater herbicidal activity of their products are:

(1) Processes wherein M is an ammonium, substituted ammonium, alkali or alkaline earth metal ion.

(2) Processes of Preferred 1 wherein
R is

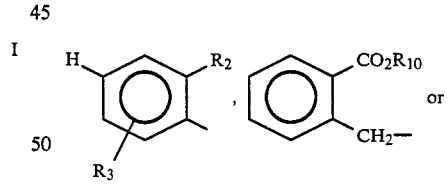

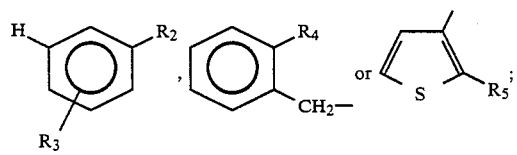

$R_2$ is Cl, $CH_3$, $SO_2N(CH_3)_2$, $S(O)_nR_8$, $CO_2R_9$, $OSO_2R_{10}$, $OR_{11}$ or $NO_2$;
$R_3$ is H, Cl, $CH_3$, $OCH_3$ or $CF_3$;
$R_8$ is $C_1$-$C_3$ alkyl, $CF_3$, $CF_2H$ or $CF_2CF_2H$;
$R_9$ is $C_1$-$C_4$ alkyl; and
$R_{11}$ is $C_1$-$C_4$ alkyl, $CF_3$, $CF_2H$ or $CF_2CF_2H$.

(3) Processes of Preferred 2 wherein the molecular sieves have a pore size of 3-5 Å.

(4) Processes of Preferred 3 wherein the solvent is a dipolar aprotic solvent.

(5) Processes of Preferred 4 wherein the solvent is N-methylpyrrolidone.

(6) Processes of Preferred 4 wherein the solvent is γ-butyrolactone.

(7) Processes of Preferred 4 wherein the solvent is triethyl phosphate.

(8) Processes of Preferred 4 wherein the molecular sieves are removed from the final formulation.

(9) Processes of Preferred 4 wherein M is lithium.

(10) Processes of Preferred 4 wherein the compound of Formula I is

2-[[(4-chloro-6-methoxypyrimidin-2-yl)aminocarbonyl]aminosulfonyl]benzoic acid, ethyl ester, lithium salt;

2-[[(4,6-dimethylpyrimidin-2-yl)aminocarbonyl]aminosulfonyl]benzoic acid, methyl ester (sulfometuron methyl), lithium salt;

2-Chloro-N-[(4-methoxy-6-methyl-1,3,5-triazin-2-yl)aminocarbonyl]benzenesulfonamide (chlorsulfuron), lithium salt;

2-[[4,6-dimethoxypyrimidin-2-yl)aminocarbonyl]aminosulfonylmethyl]benzoic acid, methyl ester, lithium salt;

N-[(4,6-dimethylpyrimidin-2-yl)aminocarbonyl]-2-hydroxybenzenesulfonamide, ethanesulfonate, lithium salt;

2-[[N-(4-methoxy-6-methyl-1,3,5-triazin-2-yl)-N-methylaminocarbonyl]aminosulfonyl]benzoic acid, methyl ester, lithium salt;

N'-[N-(4-methoxy-6-methyl-1,3,5-triazin-2-yl)-N-methylaminocarbonyl]-N,N-dimethyl-1,2-benzenedisulfonamide, lithium salt; and 3-[[(4-methoxy-6-methyl-1,3,5-triazin-2-yl)aminocarbonyl]aminosulfonyl]-2-thiophenecarboxylic acid, methyl ester, lithium salt.

The formulations made by the process of this invention have improved chemical stability and are useful as pre-emergent and post-emergent herbicides.

DETAILED DESCRIPTION OF THE INVENTION

Synthesis

This invention relates to a novel process for the preparation of homogeneous solution formulations of sulfonylureas of Formula I with improved chemical stability, by contacting said solutions with molecular sieves.

Solution formulations are desirable because of the ease with which they can be measured, poured, handled or diluted in preparation for spraying. In addition, the processes and equipment necessary for preparing solution formulations are simpler and less costly than those needed for manufacturing dry formulations or dispersions. For example, the need for expensive grinding or drying equipment is obviated when preparing solution formulations.

In a true solution system, the compounds of Formula I are susceptible to the degradative effects of moisture and impurities present in at least trace quantities in all practical solvent systems. Hence the storage stability of these formulations may be a limiting factor in their usefulness over any period of time. Due to the high herbicidal activity of the compounds of Formula I, they may be required in only low concentrations in a formulation. In this case, the stability problem may be aggravated because of the increased relative concentration of the contaminants which promote decomposition.

The sulfonylureas of Formula I can be prepared by methods known in the art; for example, see U.S. Pat. No. 4,127,405, U.S. Pat. No. 4,394,506 and U.S. Pat. No. 4,383,113, the disclosures of which are hereby incorporated by reference.

Agriculturally suitable compounds of Formula I can be prepared by a number of ways known to the art. For example, the compounds of Formula I can be made by treating the corresponding N-protonated sulfonylureas with a solution of an alkali or alkaline earth metal salt having a sufficiently basic anion (e.g., hydroxide, alkoxide, carbonate or hydride). Ammonium and quaternary amine salts can be made by similar techniques.

The compounds of Formula I can also be prepared by exchange of one cation for another. Cationic exchange can be effected by direct treatment of an aqueous solution of a salt of Formula I (e.g., an alkali metal or quaternary amine salt) with a solution containing the cation to be exchanged. This method is most effective when the desired compound of Formula I containing the exchanged cation is insoluble in water and can be separated by filtration.

Exchange may also be effected by passing an aqueous solution of a salt of a compound of Formula I (e.g., an alkali metal or quaternary amine salt) through a column packed with a cation exchange resin containing the cation to be exchanged. In this method the cation of the resin is exchanged for that of the original salt and the desired product is eluted from the column. This method is particularly useful when the desired salt is water-soluble.

It has been found that solution formulations of compounds of Formula I can be prepared with improved chemical stability of contacting said solution formulations with molecular sieves.

Molecular sieves are synthetically produced crystalline metal alumino-silicates, that have been activated for adsorption by removing their water of hydration.

In contrast to other adsorbents, the pores of any particular type of molecular sieve are precisely uniform in size and of molecular dimensions. Depending on the size of these pores, molecules may be readily adsorbed, slowly adsorbed or completely excluded. This sieve-like selectivity based on molecule size, plus a selective preference for polar or polarizable molecules give molecular sieves a high level of adsorption efficiency.

In the process of this invention, the sulfonylurea of Formula I is dissolved in a suitable nonreactive solvent which allows for a concentration of at least 0.5 weight percent. The maximum allowable concentration will vary from formulation to formulation and is limited only by the solubility of the specific active ingredient in the specific solvent employed.

The solution formulation may then be permanently stored over molecular sieves. Alternatively, the formulation may be passed through a column packed with molecular sieves. In the preferred process, the solution formulation is stirred with molecular sieves for at least several minutes, preferably for at least one hous, and is then separated from the sieves. The exact time of contact is not critical but does depend, in part, upon the quantity of molecular sieves employed; the use of larger quantities allows shorter contact times while lesser quantities require longer contact time. As is well known to one skilled in the art, molecular sieves are generally used in quantities significantly in excess of the amount required to achieve a specific result. In the process of this invention, it is likewise desirable to employ quantities of sieves in excess of that amount actually required to achieve stabilization.

Preferred molecular sieves are the types 3A, 4A and 5A with nominal pore diameters of 3 Å, 4 Å and 5 Å, respectively. Molecular sieves with larger pore diameters (e.g., type 13X) may adsorb the active ingredient or solvent molecules themselves.

In the compounds of Formula I, a wide variety of cations, M, is permissible. Preferred cations are ammonium, substituted ammonium, alkali or alkaline earth metals. More preferred are compounds of Formula I where the cation is lithium.

The non-reactive solvents of this invention are aprotic and include, but are not limited to, cyclohexanone, anisole, acetophenone, benzonitrile, acetonitrile, acetone, methyl ethyl ketone, isophorone, mesityl oxide, ethyl acetate, dichloromethane monochlorobenzene, benzaldehyde, tetrahydrofuran, ethylene dichloride, and 1,1,1-trichloroethane.

Solvents of the dipolar aprotic class, typically with dielectric constants of about 20 or more, are preferred because of their greater solubilizing power for the compounds of Formula I. Examples are nitroethane, triethyl phosphate, $\gamma$-butyrolactone, propylene carbonate, dimethylsulfoxide, dimethylacetamide, dimethylformamide, and N-methyl-pyrrolidone. N-methyl-pyrrolidone, triethyl phosphate, $\gamma$-butyrolactone and propylene carbonate are most preferred because of their low toxicity, good solubilizing power and good chemical stabilization of the active ingredient.

The solution formulation may optionally contain dissolved surfactants at concentrations ranging from about 0.1 to 60 weight %. The higher ratios of surfactant to active ingredient are sometimes desirable and can be achieved by incorporation into the formulation or by tank mixing. Among the useful surfactants used in these compositions are common nonionic wetting agents such as the polyoxyethylene alcohols, nonyl phenols, esters, diesters, and sorbitol esters, and polyoxyethylene-polyoxypropylene block copolymers.

Anionic surfactants useful in these compositions include for example, alkylnaphthalenesulfonates, alkylbenzenesulfonates, dialkylsulfosuccinates, polyoxyethylene alkylsulfosuccinates and phosphates and their salts (e.g., sodium and ammonium).

The solution formulations of this invention may be used in combination with known herbicides. Such known herbicides may be added to the solution formulation in desired amounts prior to the step of contacting the solution formulation with the molecular sieves so long as this does not interfere with chemical stability.

In the following examples, all parts are by weight unless otherwise indicated. Molecular sieves were manufactured by the Davison Chemical Division of W. R. Grace Co.; however, sieves from other manufacturers would also be suitable.

EXAMPLE 1

This example illustrates the effect of storing a solution of the sodium salt of 2-chloro-N-[(4-methoxy-6-methyl-1,3,5-triazin-2-yl)aminocarbonyl]benzenesulfonamide (chlorsulfuron) in N-methylpyrrolidone over type 4A sieves.

2-Chloro-N-[(4-methoxy-6-methyl-1,3,5-triazin-2-yl)aminocarbonyl]benzenesulfonamide, sodium salt: 5.0%

N-methylpyrrolidone: 95.0%

The sodium salt of the title compound was dissolved in the N-methylpyrrolidone using a magnetic stirrer in a flask. The solution was split into four portions of about 7 gm each.

About 2 gm of type 4A sieves were added to two of the portions in glass vials and sealed. One portion was stored in a freezer ($-6°$ C.) and the other in a 45° C. oven for 15 days. The cold storage and oven aged samples were then analyzed for active ingredient by high performance liquid chromatography.

The % Relative Decomposition after oven aging was calculated as:

$$\left( \frac{\% \text{ Active}_{freezer} - \% \text{ Active}_{45° C.}}{\% \text{ Active}_{freezer}} \right) \times 100\%.$$

The results were compared to those obtained in the two unstabilized portions, containing no molecular sieves.

| Type of Treatment | % Active Freezer | % Active 45° C. | % Relative Decomposition |
|---|---|---|---|
| Stabilized with sieves | 4.19 | 4.08 | 2.6 |
| Unstabilized (no sieves) | 4.19 | 3.87 | 7.6 |

The portions containing molecular sieves had better chemical stability than the unstabilized portions of the solution.

EXAMPLE 2

This example illustrates the effect of storing a solution of the sodium salt of 2-chloro-N-[(4-methoxy-6-methyl-1,3,5-triazin-2-yl)aminocarbonyl]benzenesulfonamide (chlorsulfuron) in $\gamma$-butyrolactone over type 4A sieves.

2-Chloro-N-[(4-methoxy-6-methyl-1,3,5-triazin-2-yl)aminocarbonyl]benzenesulfonamide, sodium salt: 5%

$\gamma$-Butyrolactone: 95%

The procedure of Example 1 was followed except that the solvent was $\gamma$-butyrolactone.

| Type of Treatment | % Active Freezer | % Active 45° C. | % Relative Decomposition after 15 days |
|---|---|---|---|
| Stabilized with sieves | 4.15 | 3.96 | 4.6 |

| Type of Treatment | % Active | | % Relative Decomposition after 15 days |
|---|---|---|---|
| | Freezer | 45° C. | |
| Unstabilized (no sieves) | 4.20 | 3.93 | 6.4 |

EXAMPLE 3

This example illustrates the effect of storing a solution of the sodium salt of 2-chloro-N-[(4-methoxy-6-methyl-1,3,5-triazin-2-yl)aminocarbonyl]benzenesulfonamide (chlorsulfuron) in N-methylpyrrolidone containing a dissolved surfactant, Brij ®78 (20 POE stearyl alcohol) over type 4A molecular sieves (POE=polyoxyethylene).

2-Chloro-N-[(4-methoxy-6-methyl-1,3,5-triazin-2-yl)aminocarbonyl]benzenesulfonamide, sodium salt: 5.0%
Brij ®78: 25.0%
N-methylpyrrolidone: 70.0%

The procedure of Example 1 was followed except that the Brij ®78 was dissolved in the N-methylpyrrolidone, followed by the sodium salt of the title compound.

| Type of Treatment | % Active | | % Relative Decomposition after 14 days |
|---|---|---|---|
| | Freezer | 45° C. | |
| Stabilized with sieves | 4.27 | 4.04 | 5.4 |
| Unstabilized (no sieves | 4.27 | 3.69 | 13.6 |

EXAMPLE 4

This example illustrates the effect of treating a solution of 2-chloro-N-[(4-methoxy-6-methyl-1,3,5-triazin-2-yl)aminocarbonyl]benzenesulfonamide (chlorsulfuron), sodium salt in N-methylpyrrolidone, containing a dissolved surfactant, Brij ®96, (10 POE-oleyl alcohol) with Type 4A and 5A sieves, then removing the sieves.

2-Chloro-N-[(4-methoxy-6-methyl-1,3,5-triazin-2-yl)aminocarbonyl]benzenesulfonamide, sodium salt: 2.3%
Brij ®96: 24.0%
N-methylpyrrolidone: 73.7%

The Brij ®96 was dissolved in the N-methylpyrrolidone, followed by the title compound, using magnetic stirring in a stoppered Erlenmeyer flask. After solution was complete, 14 gm of type 4A sieves were added to a 70 gm portion of solution, and 14 gm of type 5A sieves was added to another 70 gm portion of the solution. The solutions were slowly stirred with the molecular sieves in stoppered flasks for 2 hours. The sieves were then separated from the formulations by filtration under a nitrogen blanket. Portions of the sieve treated solutions were stored at 45° C. for 3 weeks, after which time they were analyzed for active ingredient. The results were compared to those of untreated solutions stored in a refrigerator (5° C.) and at 45° C.

| Type of Treatment | % Active | | % Relative Decomposition vs. Untreated Refrigerator Control |
|---|---|---|---|
| | Refrigerator | 45° C. | |
| Untreated Control | 2.08 | 1.34 | 35.6 |
| Stirred with 4A sieves | — | 1.92 | 7.7 |
| Stirred with 5A sieves | — | 1.91 | 8.2 |

The sieve treated solution formulations showed much better chemical stability than the untreated portions of the formulation.

EXAMPLE 5

This example is similar to Example 4, except that the surfactant was Brij ®98 (20 POE-oleyl alcohol) instead of Brij ®96.

| Type of Treatment | % Active | | % Relative Decomposition vs. Untreated Refrigerator Control after 22 days |
|---|---|---|---|
| | Refrigerator | 45° C. | |
| Untreated Control | 2.10 | 1.35 | 35.7 |
| Stirred with 4A sieves | — | 1.87 | 11.0 |
| Stirred with 5A sieves | — | 1.93 | 8.1 |

EXAMPLE 6

This example illustrates the effect of treating a high concentration of 2-[N-[(4-methoxy-6-methyl-1,3,5-triazin-2-yl)aminocarbonyl]aminosulfonyl]benzoic acid, methyl ester, sodium salt in N-methylpyrrolidone with type 4A molecular sieves, then removing the sieves.

2-[N-[(4-methoxy-6-methyl-1,3,5-triazin-2-yl)aminocarbonyl]aminosulfonyl]benzoic acid, methyl ester, sodium salt: 35%
N-methypyrrolidone: 65%

17.5 gm of the title compound was dissolved in 32.5 gm of N-methylpyrrolidone in a stoppered Erlenmeyer flask. 10 gm of Type 4A sieves were added and the solution was stirred gently with the seives for 2 hours. The solution was then filtered to remove the sieves, and portions were stored in the refrigerator and at 45° C. for 18 days.

Another solution was prepared as above, but was not treated with molecular sieves. Portions of this solution were stored in the refrigerator and at 45° C. for 23 days. Because of the different storage times for the treated and untreated solutions, stability comparisons in the following table are made on the basis of % relative decomposition per day (i.e., % relative decomposition divided by time in storage).

| Type of Treatment | % Active | | % Relative Decomposition per day vs. Control |
|---|---|---|---|
| | Refrigerator | 45° C. | |
| Untreated Control | 30.62 | 17.32 | 1.89 |

| Type of Treatment | % Active Refrigerator | 45° C. | % Relative Decomposition per day vs. Control |
| --- | --- | --- | --- |
| Sieve treated | 30.88 | 27.36 | 0.63 |

The sieve-treated high active solution formulation of 2-[N-[(4-methoxy-6methyl-1,3,5-triazin-2-yl)-aminocarbonyl]aminosulfonyl]benzoic acid, methyl ester, sodium salt had substantially better chemical stability than the untreated control solution.

EXAMPLE 7

This example illustrates the effect of treating a solution of 2-[N-[(4-methoxy-6-methyl-1,3,5-triazin-2-yl)aminocarbonyl]aminosulfonyl]benzoic acid, methyl ester, ammonium salt in propylene carbonate, with type 4A and 5A molecular sieves.

2-[N-[(4-methoxy-6-methyl-1,3,5-triazin-2-yl)aminocarbonyl]aminosulfonyl]benzoic acid, methyl ester, ammonium salt: 10.0%
Propylene carbonate 90.0%

35 gm portions of the above solution were stirred with 7 gm of type 4A and 5A sieves for 2 hours in stoppered flasks. The treated solutions were separated from the sieves by filtration under a nitrogen atmosphere. Portions of the sieve-treated solutions were stored at 45° C. for 22 days, after which time they were analyzed for active ingredient. The results were compared to those of untreated controls stored at −6° C. and at 45° C.

| Type of Treatment | % Active Freezer | 45° C. | % Relative Decomposition vs. Untreated Freezer Control |
| --- | --- | --- | --- |
| Untreated Control | 8.60 | 0.62 | 93 |
| Stirred with 4A sieves | — | 1.42 | 84 |
| Stirred with 5A sieves | — | 1.55 | 82 |

EXAMPLE 8

This example illustrates the in situ preparation of 2-chloro-N-[(4-methoxy-6-methyl-1,3,5-triazin-2-yl)-aminocarbonyl]benzenesulfonamide (chlorsulfuron), lithium salt, by reaction of the sulfonylurea with lithium carbonate in N-methylpyrrolidone followed by treatment of the solution with type 4A molecular sieves to stabilize the formulation. 36.81 gm of 2-chloro-N-[(4-methoxy-6-methyl-1,3,5-triazin-2-yl)aminocarbonyl]-benzenesulfonamide (chlorsulfuron) was dissolved in 78.73 gm of N-methylpyrrolidone. 44.6 gm of lithium carbonate was added and the mixture was stirred for 45 minutes in an open Erlenmeyer flask. During this period, gas bubbles were generated due to the evolution of carbon dioxide from the reaction of the carbonate with the sulfonylurea. The solution was then filtered to remove undissolved lithium carbonate. Approximately one-half (65 gm) of the filtered solution was stirred gently with 30 gm of type 4A sieves (previously activated at 300° C. overnight) for 4 hours. The sieves were then removed by filtration under a nitrogen blanket. A portion of the sieve-treated solution was stored at 45° C. for 3 weeks after which time it was analyzed for active ingredient. The results were compared to those of untreated controls stored at 5° C. and 45° C.

| Type of Treatment | % Active Refrigerator | 45° C. | % Relative Decomposition vs. Untreated Refrigerator Control |
| --- | --- | --- | --- |
| Untreated Control | 30.47 | 27.70 | 9.1 |
| Stirred with 4A sieves | — | 30.18 | 0.95 |

Molecular sieve treatment thus substantially improved the chemical stability of the solution formulation of 2-chloro-N-[(4-methoxy-6-methyl-1,3,5-triazin-2-yl)-aminocarbonyl]benzenesulfonamide (chlorsulfuron), lithium salt.

EXAMPLE 9

This example illustrates the in-situ preparation of 2-[N-[(4-methoxy-6-methyl-1,3,5-triazin-2yl)aminocarbonyl]aminosulfonyl]benzoic acid, methyl ester, lithium salt, by reaction of the sulfonylurea with lithium hydroxide in N-methylpyrrolidone, followed by treatment of the solution with type 5A molecular sieves to stabilize the formulation.

41.29 gm of 2-N-[(4-methoxy-6-methyl-1,3,5-triazin-2-yl)aminocarbonyl]aminosulfonyl]benzoic acid, methyl ester was dispersed in 76.22 gm of N-methylpyrrolidone in a stoppered Erlenmeyer flask. 2.49 gm of anhydrous lithium hydroxide was added and the mixture was allowed to stir overnight. After 24 hours of stirring, an additional 0.25 gm of anhydrous lithium hydroxide was added and stirred for approximately two more hours. Undissolved solids were then separated from the solution by centrifugation. Approximately half (60 gm) of the clarified solution was stirred gently with 30 gm of type 5A sieves (previously activated overnight at 300° C.) for 4 hours. The sieves were then removed by filtration under a nitrogen blanket.

A portion of the sieve-treated solution was stored at 45° C. for 3 weeks, after which time it was analyzed for active ingredient. The results were compared to those of untreated control stored at 5° C. and 45° C.

| Type of Treatment | % Active Refrigerator | 45° C. | % Relative Decomposition vs. Untreated Refrigerator Control |
| --- | --- | --- | --- |
| Untreated Control | 34.4 | 29.6 | 14.0 |
| Stirred with 5A sieves | — | 32.4 | 5.8 |

The sieve treatment improved the chemical stability of the solution formulation of 2-[N-[(4-methoxy-6-methyl-1,3,5-triazin-2-yl)aminocarbonyl]aminosulfonyl]benzoic acid, methyl ester lithium salt.

What is claimed is:

1. A process for stabilizing a solution formulation comprising a compound of Formula I dissolved in an aprotic solvent, which is subject to the degradative effects of moisture and impurities:

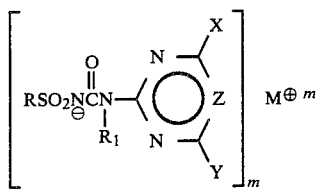

wherein
R is

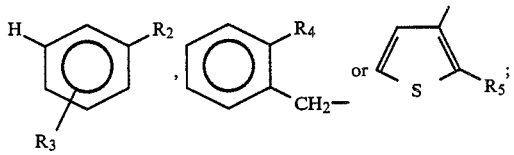

$R_1$ is H or $CH_3$;
$R_2$ is F, Cl, Br, $C_1$-$C_4$ alkyl, $SO_2NR_6R_7$, $S(O)_nR_8$, $SO_2NCH_3(OCH_3)$, $CO_2R_9$, $OSO_2R_{10}$,

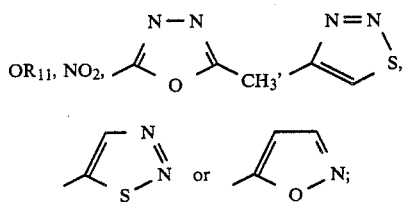

$R_3$ is H, F, Cl, Br, $CH_3$, $OCH_3$ or $CF_3$;
$R_4$ is Cl, $NO_2$ or $CO_2R_{10}$;
$R_5$ is Cl, Br, $SO_2NR_6R_7$, $S(O)_nR_{10}$ or $CO_2R_{10}$;
$R_6$ and $R_7$ are independently $C_1$-$C_3$ alkyl;
$R_8$ is $C_1$-$C_3$ alkyl or $C_1$-$C_3$ alkyl substituted by 1-5 atoms of F, Cl or Br;
$R_9$ is $C_1$-$C_4$ alkyl, $CH_2CH_2OCH_3$, $CH_2CH_2Cl$ or $CH_2CH=CH_2$;
$R_{10}$ is $C_1$-$C_3$ alkyl;
$R_{11}$ is $C_1$-$C_4$ alkyl, $CH_2CH=CH_2$, $CH_2C\equiv CH$ or $C_1$-$C_3$ alkyl substituted with 1-5 atoms of F, Cl or Br;
n is 0 or 2;
M is an agriculturally suitable cation;
m is 1, 2 or 3;
Z is CH or N;
X is $CH_3$, $OCH_3$, Cl or $OCHF_2$; and
Y is $CH_3$, $OCH_3$, $CH(OCH_3)_2$, $OCHF_2$

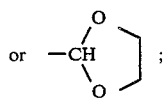

provided that when
X is Cl, then Z is CH and Y is $OCH_3$, or $OCF_2H$;
said process comprising contacting under adsorption conditions said solution formulation with molecular sieves having nominal pore diameters sized to adsorb water and to exclude the solvent and compound of Formula I, for a sufficient time to impart enhanced chemical stability to said solution formulation.

2. The process of claim 1 wherein M is an ammonium, substituted ammonium, alkali or alkaline earth metal ion.

3. The process of claim 2 wherein R is

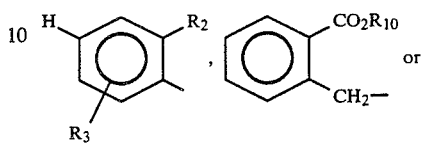

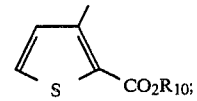

$R_2$ is Cl, $CH_3$, $SO_2N(CH_3)_2$, $S(O)_nR_8$, $CO_2R_9$, $OSO_2R_{10}$, $OR_{11}$ or $NO_2$;
$R_3$ is H, Cl, $CH_3$, $OCH_3$ or $CF_3$;
$R_8$ is $C_1$-$C_3$ alkyl, $CF_3$, $CF_2H$ or $CF_2CF_2H$;
$R_9$ is $C_1$-$C_4$ alkyl; and
$R_{11}$ is $C_1$-$C_4$ alkyl, $CF_3$, $CF_2H$ or $CF_2CF_2H$.

4. The process of claim 3 wherein said molecular sieves are crystalline metal alumino-silicates activated for adsorption by removing their water of hydration and which have a pore size of 3-5 Å.

5. The process of claim 4 wherein said solvent is a dipolar aprotic solvent.

6. The process of claim 5 wherein said dipolar aprotic solvent is selected from the group consisting of N-methylpyrrolidone, γ-butyrolactone, and triethyl phosphate.

7. The process of claim 6 wherein M is lithium.

8. The process of claim 7 wherein said compound of Formula I is 2-[[(4-chloro-6-methoxypyrimidin-2-yl)aminocarbonyl]aminosulfonyl]benzoic acid, ethyl ester, lithium salt.

9. The process of claim 7 wherein said compound of Formula I is 2-[[(4-methoxy-6-methyl-1,3,5-triazin-2-yl)aminocarbonyl]aminosulfonyl]benzoic acid, methyl ester, lithium salt.

10. The process of claim 7 wherein said compound of Formula I is 2-[[(4,6-dimethylpyrimidin-2-yl)aminocarbonyl]aminosulfonyl]benzoic acid, methyl ester, lithium salt.

11. The process of claim 7 wherein said compound of Formula I is 2-chloro-N-[(4-methoxy-6-methyl-1,3,5-triazin-2-yl)aminocarbonyl]benzenesulfonamide, lithium salt.

12. The process of claim 7 wherein said compound of Formula I is 2-[[4,6-dimethoxypyrimidin-2-yl)aminocarbonyl]aminosulfonylmethyl]benzoic acid, methyl ester, lithium salt.

13. The process of claim 7 wherein said compound of Formula I is N-[(4,6-dimethylpyrimidin-2-yl)aminocarbonyl]-2-hydroxybenzenesulfonamide, ethanesulfonate, lithium salt.

14. The process of claim 7 wherein said compound of Formula I is 2-[[(4-methoxy-6-methyl-1,3,5-triazin-2- yl)-N-methylaminocarbonyl]aminosulfonyl]benzoic acid, methyl ester, lithium salt.

15. The process of claim 7 wherein said compound of Formula I is N'-[N-(4-methoxy-6-methyl-1,3,5-triazin-2-yl)-N-methylaminocarbonyl]-N,N-dimethyl-1,2-benzenedisulfonamide, lithium salt.

16. The process of claim 7 wherein said compound of Formula I is 3-[[(4-methoxy-6-methyl-1,3,5-triazin-2-yl)aminocarbonyl]aminosulfonyl]-2-thiophenecarboxylic acid, methyl ester, lithium salt.

17. The stabilized formulation made by the process of claim 1.

18. The stabilized formulation made by the process of claim 2.

19. The stabilized formulation made by the process of claim 3.

20. The stabilized formulation made by the process of claim 4.

21. The stabilized formulation made by the process of claim 5.

22. The stabilized formulation made by the process of claim 6.

23. The stabilized formulation made by the process of claim 7.

24. The stabilized formulation made by the process of claim 8.

25. The stabilized formulation made by the process of claim 9.

26. The stabilized formulation made by the process of claim 10.

27. The stabilized formulation made by the process of claim 11.

28. The stabilized formulation made by the process of claim 12.

29. The stabilized formulation made by the process of claim 13.

30. The stabilized formulation made by the process of claim 14.

31. The stabilized formulation made by the process of claim 15.

32. The stabilized formulation made by the process of claim 16.

* * * * *